US00PP26123P3

(12) United States Plant Patent
Conev et al.

(10) Patent No.: US PP26,123 P3
(45) Date of Patent: Nov. 24, 2015

(54) DWARF GRAPEVINE 'VDG002'

(50) Latin Name: *Vitis vinifera*
Varietal Denomination: VDG002

(71) Applicant: Vineland Research and Innovations Centre Inc., Vineland Station (CA)

(72) Inventors: Rumen Conev, St. Catharines (CA); Daryl Somers, Fenwick (CA)

(73) Assignee: Vineland Research and Innovations Centre Inc., Vineland Station (CA)

( * ) Notice: Subject to any disclaimer, the term of this patent is extended or adjusted under 35 U.S.C. 154(b) by 65 days.

(21) Appl. No.: 13/999,594

(22) Filed: Mar. 12, 2014

(65) Prior Publication Data

US 2014/0359903 P1 Dec. 4, 2014

(30) Foreign Application Priority Data

Jun. 6, 2013 (CA) ..... PBR 13-8053

(51) Int. Cl.
*A01H 5/00* (2006.01)
*A01H 5/08* (2006.01)

(52) U.S. Cl.
USPC ..... Plt./207
CPC ..... *A01H 5/0812* (2013.01)

(58) Field of Classification Search
USPC ..... Plt./207
See application file for complete search history.

(56) References Cited

PUBLICATIONS

PLUTO Plant Variety Database Jul. 9, 2015.*

* cited by examiner

*Primary Examiner* — Annette Para

(57) ABSTRACT

The invention is a new and distinct ornamental dwarf grapevine variety denominated 'VDG002'. The new grapevine is characterized by having approximately half of the mid-rib veins with medium red anthocyanin color, medium red anthocyanin color for petiole, medium red anthocyanin color for young shoots, almost flat mature leaf blades, lighter green color mature leaves, a lack of the characteristic downy white appearance of leaves in the female parent 'Pixie'™, and yellow-green berries.

6 Drawing Sheets

Latin name of the genus and species of the plant claimed: *Vitis vinifera.*

Variety denomination: 'VDG002'.

BACKGROUND OF THE INVENTION

The new and distinct dwarf ornamental grapevine described and claimed herein originated from a cross between 'Pixie'™×'Cabernet Franc'.

The female parent 'Pixie'™ is a natural dwarf ornamental grapevine (*Vitis vinifera*) derived from periclinal L1/L2 chimera 'Pinot Meunier' with dark purple berry skin. 'Pixie'™ is the only known naturally dwarf grapevine in the public domain.

The pollen parent 'Cabernet Franc' is an old *Vitis vinifera* variety from France with purple berry skin.

The present variety of dwarf grapevine was first produced by controlled hybridization. The original cross was done at Vineland Research and Innovations Centre, Vineland Station, Ontario, Canada on Oct. 22, 2010.

'VDG002' was first successfully propagated asexually by single node softwood cuttings at the Vineland Research and Innovations Centre, Vineland Station, Ontario, Canada on Jun. 8, 2012. It is being maintained on its own roots in a container in a Canadian Food Inspection Agency certified greenhouse facility at Vineland Research and Innovation Centre, Vineland Station, Ontario, Canada.

SUMMARY OF THE INVENTION

The new grapevine 'VDG002' has the following major distinguishing characteristics. 'VDG002' has approximately half of the mid-rib veins with medium red anthocyanin color, whereas the mid rib veins in 'Pixie'™ are completely green. Petiole in 'VDG002' is medium red anthocyanin color, whereas the petiole in 'Pixie'™ is completely green. Young shoots in 'VDG002' are medium red anthocyanin color, whereas the shoots of 'Pixie'™ are entirely green. Mature leaf blades of 'VDG002' are almost flat, whereas the leaf blades of mature leafs in 'Pixie'™ have curly edges. Mature leaf in 'VDG002' has lighter green color, whereas mature leaf in 'Pixie'™ has dark green color. The leaves in 'VDG002' lack the very characteristic downy white appearance of leaves in 'Pixie'™, which is due to large number of fine white hairs on leaves.

The characteristics most useful in distinguishing 'VDG002' from 'Pixie'™ are young leaf: prostrate hairs between main veins on lower side of blade, shoot: color of dorsal side of internodes, shoot: color of ventral side of internodes, shoot: color of dorsal side of nodes, shoot: color of ventral side of nodes, mature leaf: proportion of main veins on upper side with anthocyanin coloration, berry: color of skin (without bloom), and berry: particular flavor.

BRIEF DESCRIPTION OF THE DRAWING

The accompanying photographic illustration illustrates in full color 'VDG002'. The colors are as nearly true as reasonably possible in color representation of this type. Colors in the photographs may differ from the color values cited in the detailed botanical description below, which accurately describes the colors of the new dwarf grapevine.

DETAILED BOTANICAL DESCRIPTION OF THE INVENTION

Figure 1:
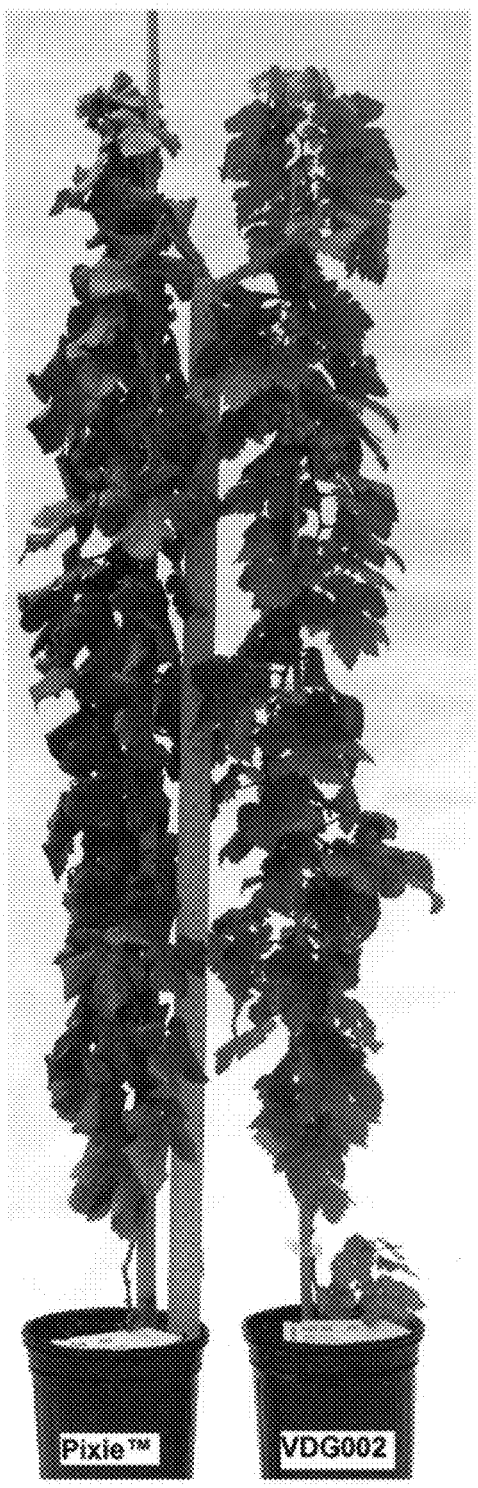
FIG. 1 shows habit and foliage color of 'VDG002', in comparison to the female parent 'Pixie'™.
Figure 2:
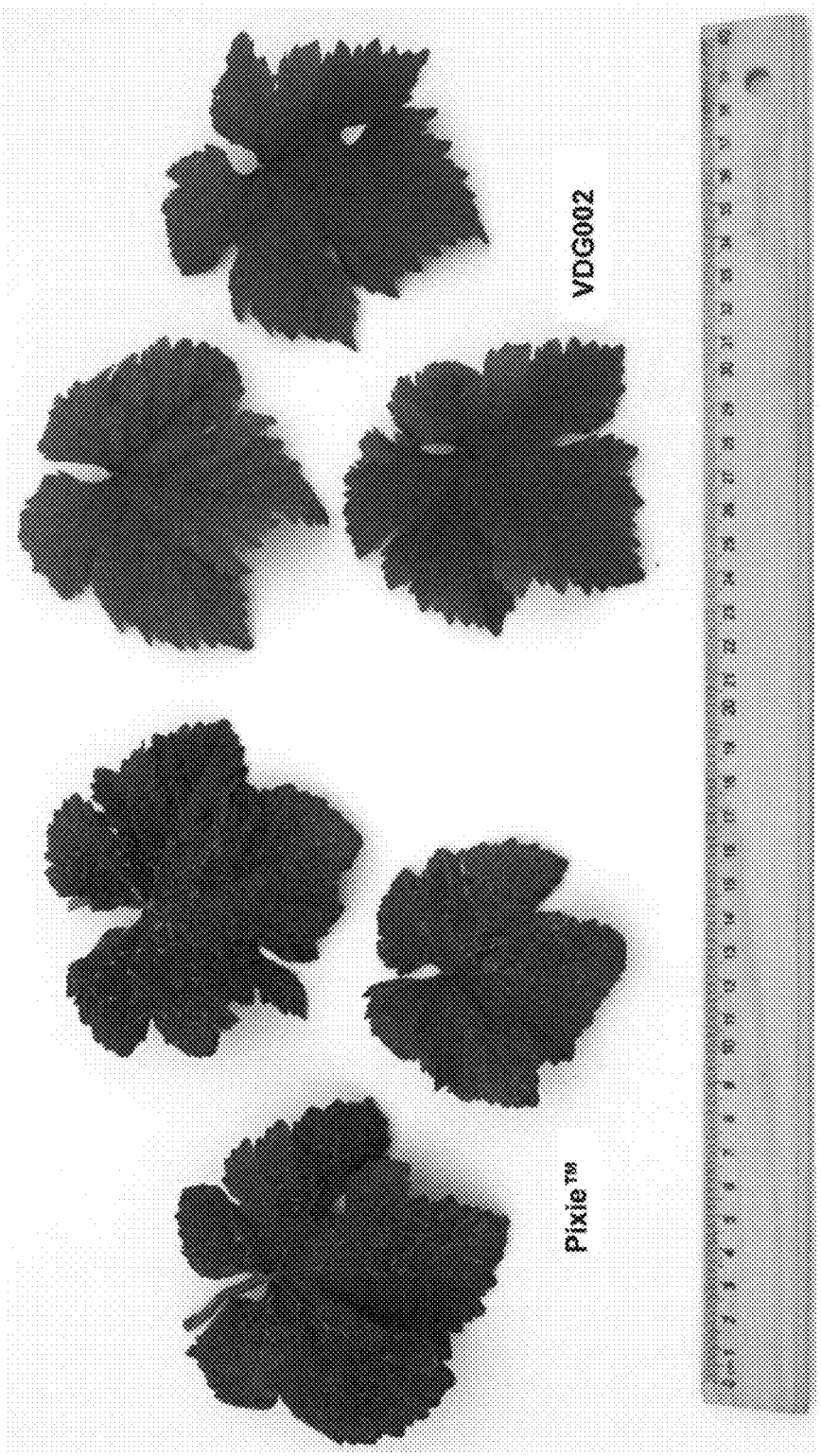
FIG. 2 shows upper side of mature leaf blades of 'VDG002', in comparison to the female parent 'Pixie'™.
Figure 3:
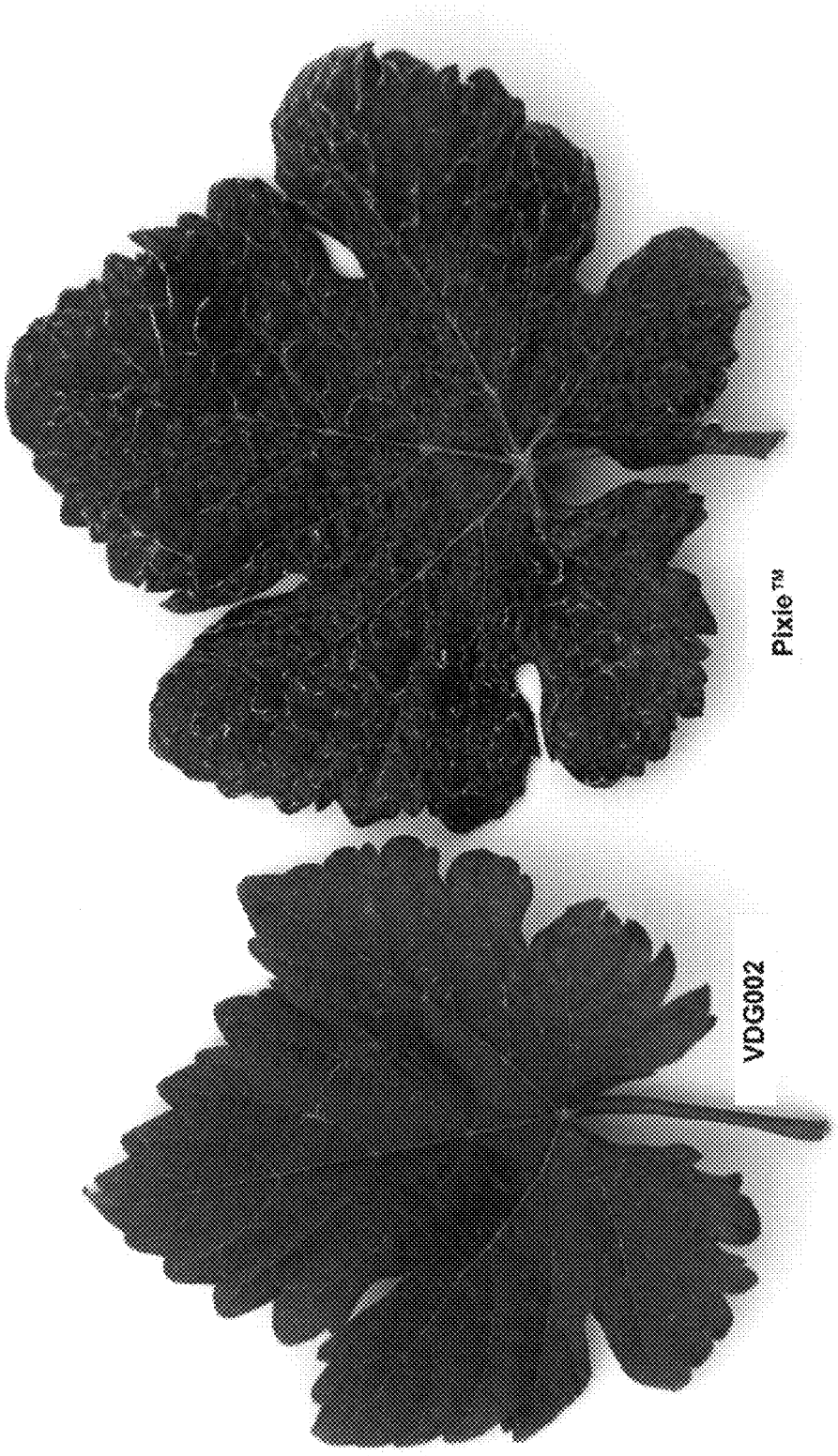
FIG. 3 shows a magnified view of upper side of mature leaf blade of 'VDG002', in comparison to the female parent 'Pixie'™.
Figure 4:
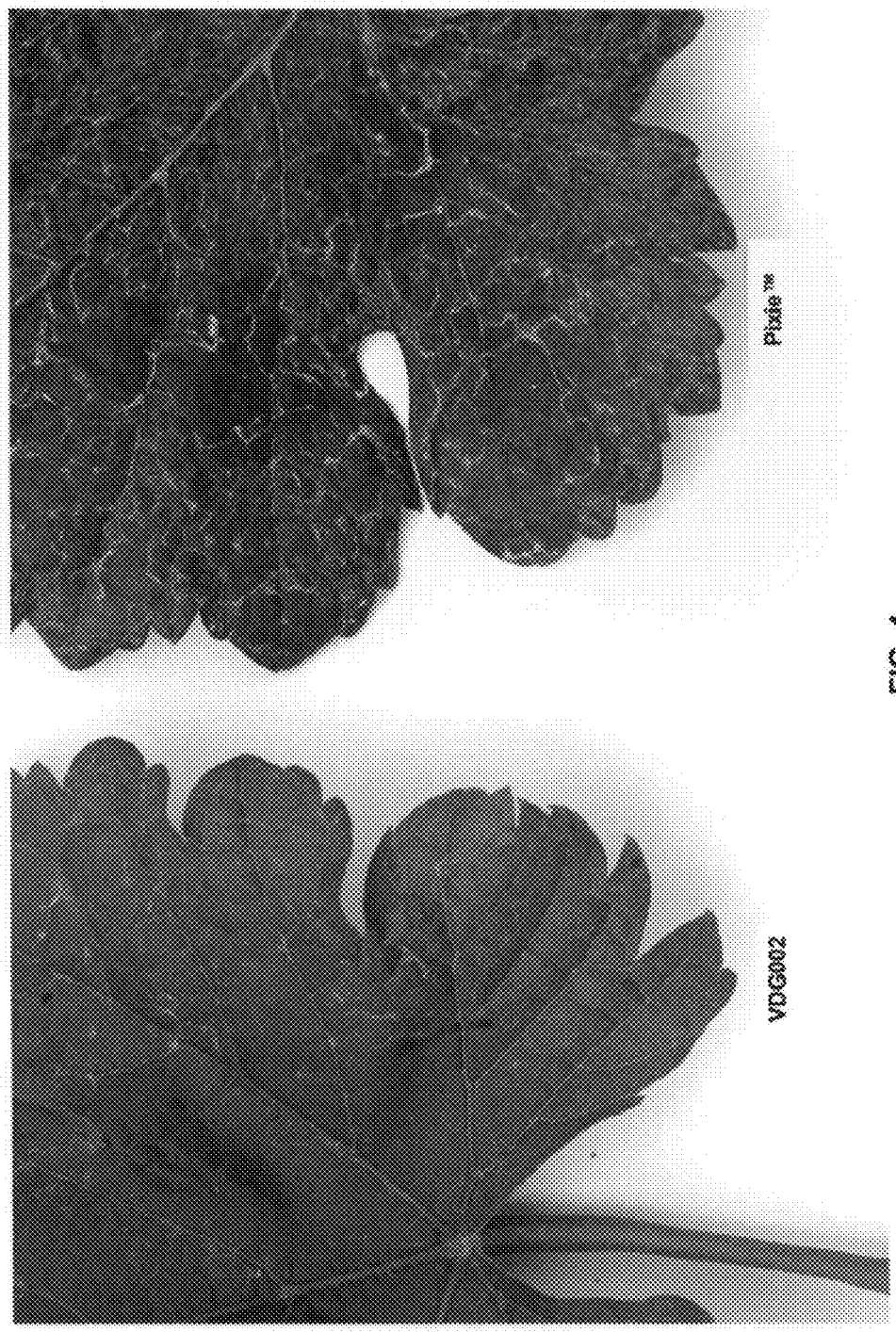
FIG. 4 shows a more magnified view of upper side of mature leaf blade of 'VDG002', in comparison to the female parent 'Pixie'™.
Figure 5:
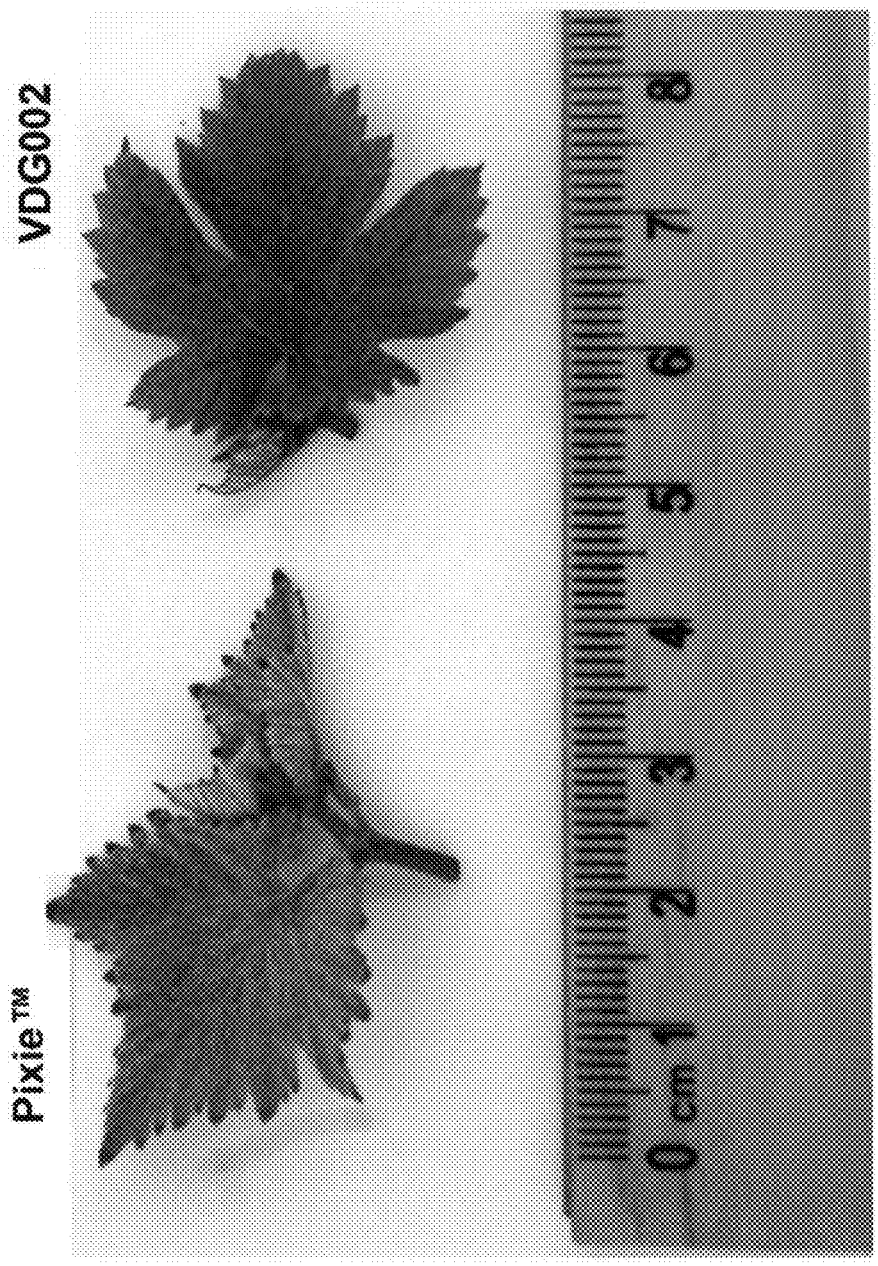
FIG. 5 shows upper side of young shoot of 'VDG002', in comparison to the female parent 'Pixie'™.
Figure 6:
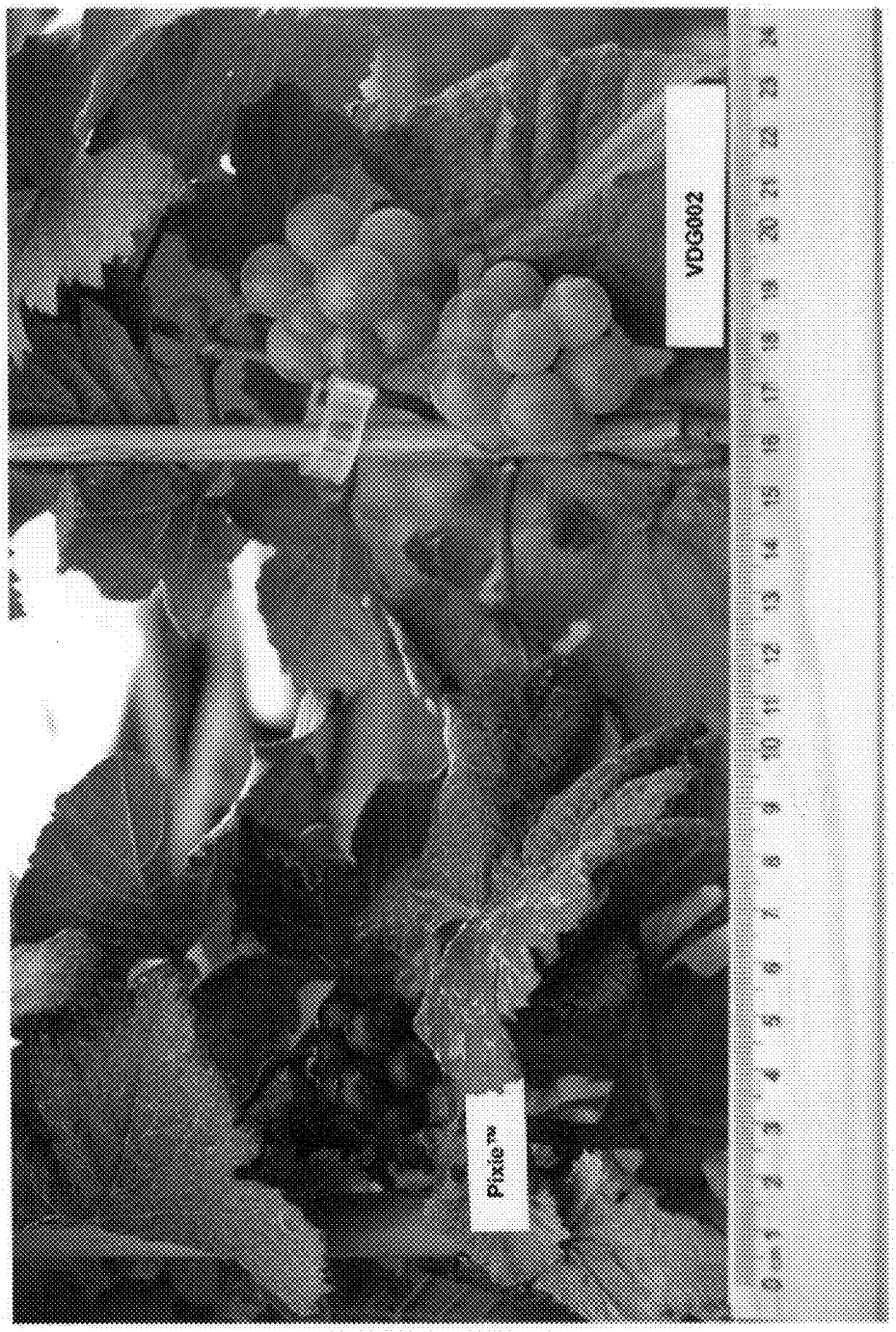
FIG. 6 shows grape bunch size and density and berry color, size and shape of 'VDG002', in comparison to the female parent 'Pixie'™.

'VDG002' is a dwarf ornamental grapevine with edible fruit. 'VDG002' has inherited the undetermined growth pattern and the dwarf growth habit from the mother variety ('Pixie'™) The internodes are 10-15 mm in length (approximately 10-20 times shorter compared to standard *Vitis vinifera* cultivars). Genotypic lab analysis confirmed the hybrid status of 'VDG002'. Polymerase chain reaction (PCR) was performed on template DNA extracted from 'VDG002' using microsatellite marker primers that were polymorphic between 'Pixie'™ and 'Cabernet Franc'. The microsatellite markers confirmed that the new variety 'VDG002' is a hybrid of the parents.

The variety is uniform and stable. No off-types, variants or mutations have been found to date.

The R.H.S. Colour Chart of The Royal Horticultural Society has been used for colour identification of foliage, berry skin and shoot. The description is based on the observation of 10 one year old plants growing in containers on their own roots in a greenhouse facility at Vineland Research and Innovation Centre, Vineland Station, Ontario, Canada during the years 2013 and 2015.

Time of bud burst: Not available as the plants were grown in a greenhouse.

Young shoot:
- *Openness of tip*.—Closed.
- *Prostrate hairs on tip*.—Very dense.
- *Anthocyanin coloration on prostrate hairs on tip*.—Absent or very weak.

Young leaf:
- *Color of upper side of blade*.—Green (137-B).
- *Prostrate hairs between main veins on lower side of blade*.—Absent or very sparse.

Shoot:
- *Color of dorsal side of internodes*.—Green (138-B).
- *Color of ventral side of internodes*.—Green (138-B).
- *Color of dorsal side of nodes*.—Green (138-B).
- *Color of ventral side of nodes*.—Green (138-B).
- *Length of tendril*.—Very short (very scarce, very short, decline fast).

Flower:
- *Sexual organs*.—Fully developed stamens and fully developed gynoecium.

Inflorescence:
- *Type*.—Hermaphrodite.
- *Date of bloom*.—Continuous.
- *Flower cap*.—5 fused, green (138-A).
- *Flowers/cluster*.—10-110.
- *Flower diameter*.—About 2 mm.
- *Cluster length+peduncle*.—About 4-5 cm.
- *Pistil length*.—About 2.2 mm.
- *Pistil color*.—Yellow green (146-B).
- *Filament length*.—1-2 mm.

Mature leaf:
- *Size of blade*.—Small to very small.
- *Shape of blade*.—Circular.
- *Blistering of upper side of blade*.—Strong.
- *Number of lobes*.—Five.
- *Depth of upper lateral sinuses*.—Deep to medium.
- *Arrangement of lobes of upper lateral sinuses*.—Slightly overlapped.
- *Arrangement of lobes of petiole sinus*.—Strongly overlapped.
- *Length of teeth*.—Medium.
- *Ratio length/width of teeth*.—Medium.
- *Shape of teeth*.—Both sides convex.
- *Proportion of main veins on upper side with anthocyanin coloration*.—Low.
- *Prostrate hairs between main veins on lower side of blade*.—Absent or very sparse.
- *Erect hairs on main veins on lower side of blade*.—Absent or very sparse.
- *Length of petiole compared to length of middle vein*.—Much shorter.
- *Color of upper surface*.—Green (N137-A).

Time of beginning of berry ripening: Not available as the plants were grown in a greenhouse.

Bunch:
- *Size (peduncle excluded)*.—Small to very small.
- *Density*.—Very dense to dense.
- *Length of peduncle of primary bunch*.—Medium.

Berry:
- *Size*.—Medium to small.
- *Shape*.—Globose.
- *Color of skin (without bloom)*.—Yellow-green (152-C).
- *Ease of detachment from pedicel*.—Moderately easy.
- *Thickness of skin*.—Medium.
- *Anthocyanin coloration of flesh*.—Absent or very weak.
- *Firmness of flesh*.—Moderately firm.
- *Particular flavor*.—Other than muscat, foxy or herbaceous.
- *Formation of seeds*.—Complete.

Woody shoot:
- *Main color*.—Orange brown (175-C).

Other: The petiole in 'VDG002' has medium red anthocyanin colour, while the petiole in 'Pixie'™ is completely green. Mature leaf blades of 'VDG002' are almost flat, while the leaf blades of mature leaf blades in 'Pixie'™ have curly edges. 'VDG-002' has no particular resistance to any disease or insects and its susceptibility to disease and insects is similar to that of the female parent "Pixie"™.

Biometric data of 'VDG002' is compared to that of the mother variety ('Pixie'™) in Table 1.

TABLE 1

| Biometric data | 'VDG002' | 'Pixie' ™ |
|---|---|---|
| Average size of mature leaf blade, L × W, mm | 106 × 110 | 106 × 107 |
| Length of petiole/length of main vein, mm | 31/74 | 42/77 |
| Height of central stem, cm | 114 | 98 |
| Total linear growth per plant, cm | 120 | 150 |
| Total number of nodes per plant | 91 | 117 |
| Average internode size, mm | 13 | 13 |
| First bunch set at node number | 43 | 25 |
| Average peduncle length, mm | 37.0 | 40.5 |
| Average number of berries per bunch | 19.1 | 21.6 |
| Average bunch weight, g | 28.8 | 18.9 |
| Average berry weight, g | 1.5 | 0.9 |
| Average berry size, mm | 16.4 | 12.7 |

TABLE 1-continued

| Biometric data | 'VDG002' | 'Pixie' ™ |
|---|---|---|
| Average number of seeds/berry | 1.2 | 2.7 |
| Sugar content, °Bx | 22.7 | 21.3 |

The 'VDG002' variety has not been observed under all possible environmental conditions to date. Accordingly, it is possible that the phenotypic expression may vary somewhat with changes in light intensity and duration, cultural practices, and other environmental conditions.

What is claimed:

1. A new and distinct variety of dwarf ornamental grapevine substantially as herein illustrated and described.

* * * * *